United States Patent [19]
Koola

[11] Patent Number: 6,140,398
[45] Date of Patent: Oct. 31, 2000

[54] SALICYLIC ACID DIPHOSPHATES FOR USE AS FLAME RETARDANT MATERIALS

[75] Inventor: Johnson D. Koola, Nashville, Tenn.

[73] Assignee: Rhodia Inc., Cranbury, N.J.

[21] Appl. No.: 09/348,909

[22] Filed: Jul. 7, 1999

Related U.S. Application Data

[60] Provisional application No. 60/092,258, Jul. 10, 1998.

[51] Int. Cl.$^7$ .................................................. C08K 5/52
[52] U.S. Cl. ...................... 524/121; 524/122; 524/123; 524/128; 524/132; 524/145
[58] Field of Search ........................ 428/375; 528/167; 524/121, 122, 123, 127, 128, 131, 132, 141, 145

[56] References Cited

U.S. PATENT DOCUMENTS 3,789,091  1/1974  Anderson et al. .................. 260/927 R
5,614,573  3/1997  Sano et al. ............................. 524/121

*Primary Examiner*—Edward J. Cain
*Assistant Examiner*—Katarzyna Wyrozebski
*Attorney, Agent, or Firm*—Andrew M. Solomon

[57] ABSTRACT

A novel composition of matter comprising the reaction product of a phosphoryl compound, a salicylic acid derivative, and an organic compound containing two groups having hydroxyl functionality is provided. This composition has utility as a fire retardant chemical.

3 Claims, No Drawings

SALICYLIC ACID DIPHOSPHATES FOR USE AS FLAME RETARDANT MATERIALS

This application claims the benefit of the disclosure of U.S. Provisional Patent Application Ser. No. 60/092,258, filed on Jul. 10, 1998.

BACKGROUND OF THE INVENTION

1. Field of the Invention

The present invention relates to the synthesis and use of salicylic acid diphosphates for use as flame retardant materials. More specifically, the materials are produced by the synthesis of methyl salicylate, $POCl_3$ and either (a) bisphenol-A; (b) resorcinol; or (c) hydroquinone. The materials can be used to provide flame retardancy to any materials in which fire retardancy is desired, particularly to fibrous materials and plastics.

2. Technology Description

Although fiber materials composed of polyester-based synthetic fibers possess a variety of excellent physical and chemical properties, a common drawback is their tendency to combust, for which reason such polyester-based synthetic fiber materials have traditionally been subjected to finishing treatment for flame retardancy.

To impart flame retardancy to polyester-based synthetic fiber materials by finishing treatment as mentioned above, the prior art teaches the use of halogen compounds as flame retardant compounds, and flame retardancy has been imparted to polyester-based synthetic fiber materials by finishing treatment with such halogen compounds.

Here, bromine- and chlorine-containing compounds are known to be particularly effective as halogen compounds, and finishing treatment with these halogen compounds on polyester-based synthetic fiber materials typically involves dissolving a halogen-containing compound such as a halogenated cycloalkane, specifically hexabromocyclododecane, in a solvent, or using a dispersing agent or the like for its emulsification and dispersion in water, in combination with other additives when necessary, to prepare a treatment solution which is then applied to the polyester-based synthetic fiber materials mentioned above by a method such as coating, immersion or spraying.

However, when a halogen compound is applied to a polyester-based synthetic fiber material in this manner for flame retardancy, harmful halide gas is generated in the event of combustion of the polyester-based synthetic fibers, thus having an adverse effect on the environment, and therefore in recent years restrictions have been imposed on such halogen compounds.

In light of this, as alternative flame retardant compounds instead of the above-mentioned halogen compounds, the prior art has also employed phosphorus-containing compounds such as phosphoric esters and the like to impart flame retardancy to polyester-based synthetic fiber materials.

Here, the phosphorus-containing compounds which have traditionally been in common use as flame retardant compounds have low phosphorus contents and molecular weights usually as low as 200–400, and tend to degrade and volatilize at lower than the inflammation point of polyester-based synthetic fibers; consequently, they cannot impart flame retardancy to the polyester-based synthetic fiber materials as adequately as the above-mentioned halogen compounds, and thus such phosphorus compounds have had to be applied in large amounts in order to impart satisfactory flame retardancy to polyester-based synthetic fiber materials.

However, application of large amounts of these phosphorus compounds tends to cause trouble during the treatment, and when applied in large amounts phosphorus compounds result in an inferior hand of the polyester-based synthetic fiber materials.

Furthermore, when such phosphorus compounds are applied to polyester-based synthetic fiber materials, they gradually migrate through the surface of the polyester-based synthetic fiber materials with the passing of time, and their migration is accompanied by that of disperse dyes added for dyeing of the polyester-based synthetic fiber materials and dissolved in the phosphorus compounds, resulting in the problem known as "bleeding to surface" which lowers the color fastness.

U.S. Pat. No. 5,614,573 discloses a new class of materials proposed for use as fire retardants and are obtained by reacting phosphoryl compounds such as phosphorus oxychloride and phenylphosphonic dichloride, with salicylic acid derivatives, phthalic acid derivatives, dihydroxydiphenylsulfone derivatives or dihydroxydiphenylpropane derivatives. In the embodiment where the use of salicylic acid derivatives of phosphoryl compounds are suggested for use, the resulting composition is a monophosphate. To the extent necessary for completion of this disclosure, the contents of this patent is expressly incorporated by reference.

Despite the above teachings, there still exists a need in the art for improved fire retardant chemicals.

BRIEF SUMMARY OF THE INVENTION

In accordance with the present invention novel compounds and their use as fire retardants on substances requiring fire retardancy are provided. More specifically, these compounds are diphosphate derivatives of salicylic acid derivatives.

One embodiment of the present invention is directed to a novel composition of matter comprising the reaction product of a phosphoryl compound, a salicylic acid derivative, and an organic compound containing two groups having hydroxyl functionality.

In a preferred embodiment of the present invention, the composition is the reaction product of (1) methyl salicylate; (2) phosphorus oxychloride ($POCl_3$); and (3) a compound selected from the group consisting of (a) bisphenol-A; (b) resorcinol; and (c) hydroquinone.

Another embodiment of the present invention comprises a method for providing fire retardancy to a substrate by applying to the surfaces of a substrate a fire retardancy effective amount of diphosphate derivatives of salicylic acid derivatives, and more specifically the reaction product of (1) methyl salicylate; (2) phosphorus oxychloride ($POCl_3$); and (3) a compound selected from the group consisting of (a) bisphenol-A; (b) resorcinol; and (c) hydroquinone. In particularly preferred embodiments, the substrate is either fibrous (natural or synthetic fibers) or plastic.

Still another embodiment of the present invention comprises an article of manufacture having improved fire retardancy comprising a substrate and a surface coating for said substrate, wherein said surface coating is a diphosphate derivative of salicylic acid derivatives, and more specifically the reaction product of (1) methyl salicylate; (2) phosphorus oxychloride ($POCl_3$); and (3) a compound selected from the group consisting of (a) bisphenol-A; (b) resorcinol; and (c) hydroquinone. In particularly preferred embodiments, the substrate is either fibrous (natural or synthetic fibers) or plastic.

An object of the present invention is to provide a novel composition having utility as a fire retardant.

Still another object of the present invention is to provide a process for imparting fire retardancy to a substrate by applying to the substrate the novel composition of the present invention.

A further object of the present invention is to provide fire retardant materials wherein their fire retardancy is obtained as a result of applying the novel composition of the present invention thereon.

These, and other objects, will readily be apparent to those skilled in the art as reference is made to the detailed description of the preferred embodiment.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

The invention is directed to novel diphosphate compositions and more specifically diphosphate derivatives of salicylic acid derivatives. The compositions are produced by reacting a phosphoryl compound with a salicylic acid derivative and an organic compound containing two groups having hydroxyl functionality.

The phosphoryl compound is preferably of the formula $POX_3$, wherein X is a halogen atom. In preferred embodiments, X is either a Cl or Br atom, and more preferably a Cl atom. Also considered for use is phenylphosphonic dichloride.

The salicylic acid derivative is preferably an alkyl ester of salicylic acid, and more preferably of the class alkyl salicylate, wherein alkyl represents a straight chain, branched chain, cyclic or aromatic group containing between 1 and about 12 carbon atoms. Particularly preferred is the selection of straight chain hydrocarbons having three or less carbon atom, i.e., methyl salicylate, ethyl salicylate or propyl salicylate. The use of phthalic acid derivatives, dihydroxydiphenylsulfone derivatives or dihydroxydiphenylpropane derivatives as substitutes for salicylic acid derivatives are also specifically contemplated as falling within the scope of the present invention.

The third component used to form the novel composition of the present invention comprises an organic compound containing two groups having hydroxyl functionality. Examples of such compounds include bisphenol-A, resorcinol and hydroquinone.

Particularly preferred compositions include the following:
Bisphenol-A bis(methyl salicyl)diphosphate of the formula:
Resorcinol bis(methyl salicyl) diphosphate of the formula:
Hydroquinone bis(methyl salicyl) diphosphate of the formula:

Production of the novel composition is obtained by a simple reaction of the individual components, preferably in the presence of a catalyst. It is particularly preferred that stoichiometric amounts of each of the reactants are selected so that a maximum amount of diphosphate composition is produced. The catalyst selected is preferably triethyl amine. Other catalysts which may be selected include, but are not limited to, magnesium chloride, boron trifluoride, diethyl etherate, titanium tetrabutoxide and the like. Reaction can take place in a solvent, such as toluene or in the absence of a solvent.

The novel compositions have functionality as a fire retardant. In practice, it is applied to all external surfaces of a substrate for which fire retardancy is desired. Examples of substrates which may be treated include natural and synthetic fibers and plastics. The amount of novel composition to be applied is that which imparts sufficient fire retardancy to the substrate. Determination of this amount is deemed to be within the skill of the artisan.

For treatment of fibers, it is recommended that the inventive composition be coated onto the surfaces of the fibers in an amount ranging from about 0.1 to about 15 percent by weight of the fibers. The application of the composition to fiber material may be accomplished by the immersion heating method and may be performed before, during or after dyeing of the fiber material. There are fewer process steps if it is performed during the dyeing, and thus operation efficiency may be improved.

For incorporation with plastic substrates, the inventive composition can either be coated onto the surfaces or directly compounded with the polymeric materials prior to molding. The inventive composition may be added in amounts up to about 20 percent by weight of the final product.

The invention is described in greater detail by the following non-limiting examples.

EXAMPLE 1

Preparation of Bisphenol-A bis(methyl salicyl) diphosphate
Method A

A mixture of 115 g bisphenol A and 102 g triethyl amine dissolved in 500 mL toluene is reacted with 153 g phosphorus oxychloride under stirring at room temperature. After 3 hours of reaction time, a mixture of 300 g of methyl salicylate and 200 g of triethyl amine and 500 mL toluene is added to the reaction mixture over a period of 1 hour. At the end of the reaction, the reaction mixture is kept stirred at 100° C. for 12 hours. The reaction mixture is then cooled to room temperature and filtered. The residue is washed with toluene. The filtrate and washings are combined and the solvents removed. The residual product is redissolved in 500 mL of toluene and washed with 10% sodium carbonate solution. Toluene solution is dried again to collect the product as a pale yellow viscous oil.

Method B

A mixture of 58 g of bisphenol A, 115 g phosphorus oxychloride and 250 mg magnesium chloride is allowed to react at 150° C. under stirring for 12 hours. At the end of the reaction, excess phosphorus oxychloride is distilled off from the reaction mixture. 180 g of methyl salicylate and 250 mg magnesium chloride are added to the distillation residue and the reaction is continued at 150° C. for 12 hours. At the end of the reaction, the crude product is dissolved in 500 mL toluene and washed with 10% sodium carbonate solution. Toluene solution is finally dried to obtain the product as a pale yellow viscous liquid.

EXAMPLE 2

Preparation of Resorcinol bis(methyl salicyl) diphosphate

A mixture of 11 g of resorcinol, 60 g phosphorus oxychloride and 95 mg magnesium chloride is allowed to react at 140° C. under stirring for 12 hours. At the end of the reaction, excess phosphorous oxychloride is removed by distillation. A mixture of 61 g of methyl salicylate , 42 g triethylamine and 40 mL toluene is then added to the distillation residue. The reaction is then continued at 130° C. for 2 hours. The reaction product is filtered and the residue is washed with toluene. Toluene filtrate and washings are combined and dried to remove the solvent. The crude product is redissolved in 200 mL toluene and washed with 10% sodium carbonate solution. Toluene solution is finally dried to obtain the product as a pale brown viscous liquid.

EXAMPLE 3

Preparation of Hydroquinone bis(methyl salicyl) diphosphate

This diphosphate is prepared by the method of Example 2 described above except that hydroquinone is used instead of resorcinol.

Test Data

Evaluation of Bisphenol-A bis(methyl salicyl) diphosphate (Example 1 composition) as a flame retardant in plastics.

1. Polycarbonate/acrylonitrile/butadiene/styrene plastic is compounded with 16% bisphenol-A methyl salicyl diphosphate (Example 1 composition) and 0.5% Teflon powder in a batch mixture. The compounded plastic is then compression molded to obtain ⅛ and 1/16 inch thick test plaques. The plaques are subjected to the UL-94 flame test (Underwriters Laboratory). To the extent necessary for completion, the testing methodology as defined by Underwriters Laboratory for method UL-94 is expressly incorporated by reference. The compounded plastic is rated V-2.

2. Polyphenylene oxide plastic is compounded with 18% bisphenol A bis(methyl salicyl) diphosphate (Example 1 composition) in a batch mixture. The compounded plastic is then compression molded to obtain ⅛ and 1/16 inch thick test plaques. The plaques are subjected to the UL-94 flame test. ⅛ inch thick plaques are rated V-1 and 1/16 inch thick plaques are rated V-2.

Having described the invention in detail and by reference to the preferred embodiments thereof, it will be apparent that modifications and variations are possible without departing from the scope of the appended claims.

What is claimed is:

1. A composition of matter comprising the reaction product of (a) phosphoryl compound selected from the group consisting of phenylphosphonic dichloride and a compound of the formula $POX_3$ wherein X is a halogen atom, (b) a straight, branched or cyclic alkyl or aromatic ester of salicylic acid and (c) an organic compound containing two groups having hydroxyl functionality selected from the group consisting of bisphenol A, hydroquinone and resorcinol and wherein the reaction product comprises a compound selected from the group consisting of:

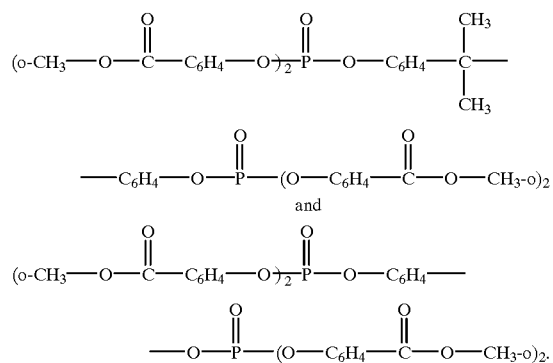

2. A process for providing fire retardancy to a substrate comprising the step of applying to the external surfaces of said substrate a fire retardancy effective amount of a composition comprising the reaction product of (a) a phosphoryl compound selected from the group consisting of phenylphosphonic dichloride and a compound of the formula $POX_3$ wherein X is a halogen atom, (b) a straight, branched or cyclic alkyl or aromatic ester of salicylic acid, and (c) an organic compound containing two groups having hydroxyl functionality selected form the group consisting of bisphenol A, hydroquinone and resorcinol and wherein the reaction product comprises a compound selected from the group consisting of:

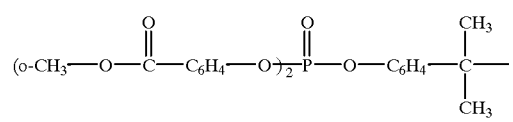

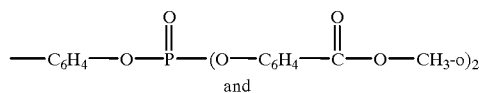

and

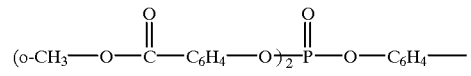

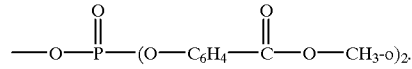

3. An article of manufacture having improved fire retardancy comprising a substrate having its external surfaces coated thereon with a fire retardancy effective amount of a composition comprising the reaction Product of (a) a phosphoryl compound selected form the group consisting of phenylphosphonic dichloride and a compound of the formula $POX_3$ wherein X is a halogen atom, (b) a straight, branched or cyclic alkyl or aromatic ester of salicylic acid, and (c) an organic compound containing two groups having hydroxyl functionality selected from the group consisting of bisphenol A, hydroquinone and resorcinol, and wherein the reaction product comprises a compound selected from the group consisting of:

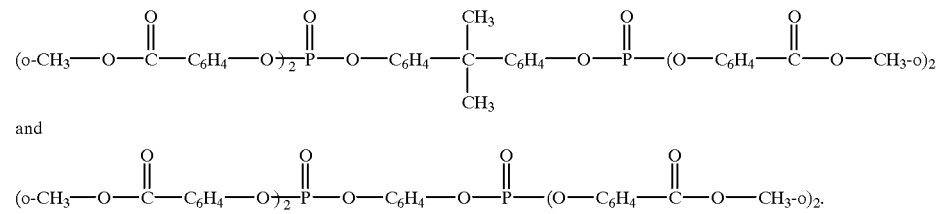

* * * * *